(12) United States Patent
Zinovik et al.

(10) Patent No.: US 12,035,746 B2
(45) Date of Patent: *Jul. 16, 2024

(54) AEROSOL-GENERATING DEVICE WITH REDUCED LEAKAGE

(71) Applicant: Altria Client Services LLC, Richmond, VA (US)

(72) Inventors: Ihar Nikolaevich Zinovik, Peseux (CH); Guillaume Frederick, Les-Geneveys-sur-Coffrane (CH); Irene Taurino, Lausanne (CH)

(73) Assignee: Altria Client Services LLC, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/316,337

(22) Filed: May 12, 2023

(65) Prior Publication Data

US 2023/0276839 A1 Sep. 7, 2023

Related U.S. Application Data

(63) Continuation of application No. 17/693,657, filed on Mar. 14, 2022, now Pat. No. 11,684,082, which is a
(Continued)

(30) Foreign Application Priority Data

Jan. 30, 2018 (EP) ..................................... 18154263

(51) Int. Cl.
*A24F 7/00* (2006.01)
*A24D 1/04* (2006.01)
(Continued)

(52) U.S. Cl.
CPC ................ *A24D 1/042* (2013.01); *A24F 7/00* (2013.01); *A24F 40/485* (2020.01); *F16K 1/14* (2013.01);
(Continued)

(58) Field of Classification Search
None
See application file for complete search history.

(56) References Cited

U.S. PATENT DOCUMENTS 9,549,573 B2 1/2017 Monsees et al.
2013/0306064 A1 11/2013 Thorens et al.
(Continued)

FOREIGN PATENT DOCUMENTS

CN 103237469 A 8/2013
CN 204409583 U 6/2015
(Continued)

OTHER PUBLICATIONS

Office Action dated Oct. 26, 2023 issued in related Japanese patent application No. 2020-538590.
(Continued)

*Primary Examiner* — Cynthia Szewczyk
(74) *Attorney, Agent, or Firm* — Harness, Dickey & Pierce, P.L.C.

(57) ABSTRACT

An aerosol-generating device includes a housing having a first end defining a mouthpiece, a second end, and a cavity defined between the first end and the second end. The device also includes a reservoir within the cavity. The reservoir is configured to store a liquid aerosol-forming substrate. The device also includes an atomizer and a valve within the mouthpiece of the housing. The valve has a first side and an second side. The second side of the valve includes a hydrophilic coating, a hydrophobic coating, or both a hydrophilic coating and a hydrophobic coating.

14 Claims, 4 Drawing Sheets

Related U.S. Application Data continuation of application No. 16/260,452, filed on Jan. 29, 2019, now Pat. No. 11,297,877, which is a continuation of application No. PCT/EP2018/085491, filed on Dec. 18, 2018.

(51) Int. Cl.
*A24F 40/485* (2020.01)
*F16K 1/14* (2006.01)
*F16K 7/06* (2006.01)
*F16K 7/16* (2006.01)
*A24F 40/10* (2020.01)

(52) U.S. Cl.
CPC .................. *F16K 7/06* (2013.01); *F16K 7/16* (2013.01); *A24F 40/10* (2020.01)

(56) References Cited

U.S. PATENT DOCUMENTS

| | | |
|---|---|---|
| 2014/0008352 A1 | 1/2014 | Uemura et al. |
| 2014/0202454 A1 | 7/2014 | Buchberger |
| 2015/0157054 A1 | 6/2015 | Liu |
| 2015/0173422 A1 | 6/2015 | Liu |
| 2015/0201674 A1 | 7/2015 | Dooly et al. |
| 2016/0143360 A1 | 5/2016 | Sanchez et al. |
| 2016/0150824 A1 | 6/2016 | Memari et al. |
| 2016/0150828 A1 | 6/2016 | Goldstein et al. |
| 2017/0042244 A1 | 2/2017 | Batista |
| 2017/0099878 A1 | 4/2017 | Murison et al. |
| 2017/0172210 A1 | 6/2017 | Bright et al. |
| 2017/0188629 A1 | 7/2017 | Dickens et al. |
| 2017/0258138 A1 | 9/2017 | Rostami et al. |
| 2018/0020730 A1 | 1/2018 | Alarcon et al. |

FOREIGN PATENT DOCUMENTS

| | | |
|---|---|---|
| CN | 204409585 U | 6/2015 |
| CN | 105963833 A | 9/2016 |
| CN | 106102489 A | 11/2016 |
| EP | 2460422 A1 | 6/2012 |
| JP | 2014-504852 A | 2/2014 |
| JP | 2014-522650 A | 9/2014 |
| JP | 5778867 B2 | 9/2015 |
| KR | 2016-0080551 A | 7/2016 |
| RU | 2012144805 A | 4/2014 |
| WO | WO-9712639 A1 | 4/1997 |
| WO | WO-2017/037457 A1 | 3/2017 |
| WO | WO-2017/055584 A1 | 4/2017 |
| WO | WO-2017113106 A1 | 7/2017 |
| WO | WO-2017/220273 A1 | 12/2017 |
| WO | WO-2018050449 A1 | 3/2018 |

OTHER PUBLICATIONS

Office Action dated Aug. 17, 2023 issued in related Chinese patent application No. 201880085711.X.
Notice of Allowance dated Oct. 9, 2023 issued in related Chinese patent application No. 201880085711.X.
Office Action dated Jul. 6, 2023 issued in related Korean patent application No. 10-2020-7021903.
Extended European Search Report for U.S. Appl. No. 18/154,263 Published Jul. 24, 2018.
International Search Report and Written Opinion for corresponding Application No. PCT/EP2018/085491 dated Mar. 27, 2019.
Written Opinion of the International Preliminary Exam Authroity for corresponding Application No. PCT/EP2018/085491, dated Jan. 10, 2020.
International Preliminary Report on Patentability for Application No. PCT/EP2018/085491, dated Apr. 21, 2020.
Russian Office Action and Search Report dated Dec. 20, 2021 for corresponding Russian Application No. 2020125305, and English-language translation thereof.
Russian Notice of Allowance dated May 12, 2022 for corresponding Russian Application No. 2020125305,a nd English-language translation thereof.
Brazilian Office Action dated Jul. 21, 2022 for corresponding Brazilian Application No. 1120200126772, and English-language translation thereof.
European Communication dated Sep. 30, 2022 for corresponding European Application No. 18826607.6.
Office Action dated Jan. 12, 2023 issued in related Japanese patent application No. 2020-538590.
Office Action dated May 25, 2023 issued in related Japanese patent application No. 2020-538590.
Notice of Allowance dated Jan. 8, 2024 issued in related Korean patent application No. 10-2020-7021903.

AEROSOL-GENERATING DEVICE WITH REDUCED LEAKAGE

CROSS-REFERENCE TO RELATED APPLICATIONS

This application is a continuation of U.S. application Ser. No. 17/693,657, filed on Mar. 14, 2022, which is a continuation of U.S. application Ser. No. 16/260,452, filed on Jan. 29, 2019, which is a continuation of, and claims priority to, international application no. PCT/EP2018/085491, filed on Dec. 18, 2018, and further claims priority under 35 U.S.C. § 119 to European Patent Application No. 18154263.0, filed Jan. 30, 2018, the entire contents of each of which are incorporated herein by reference.

BACKGROUND

Field

Example embodiments relate to an aerosol-generating device configured to heat an aerosol-forming substrate to form an inhalable aerosol. Example embodiments relate to an aerosol-generating device that is configured to reduce and/or minimize leaking of liquid aerosol-forming substrate or condensates.

Description of Related Art

Devices for generating aerosols for inhalation heat a liquid to vaporize the liquid and produce an aerosol. Such devices typically include a liquid storage portion or reservoir for holding a supply of a liquid aerosol-forming substrate, or "e-liquid", and a heater for heating the e-liquid to generate an aerosol. Such devices also include an airflow path in communication with the heater so that the aerosol can be conveyed along the airflow path and delivered to a user.

The quality of the aerosol generated by known devices can be assessed using a number of different factors. Factors may include the quantity of aerosol generated, the density of droplets within the aerosol, temperature of the aerosol, and speed of delivery of the aerosol. The quality of the experience provided by known devices may be assessed using a number of different factors. These factors may include the quality of aerosol generated as well as frequency of liquid leaking from the device.

Liquid leaking from an aerosol generating device could be e-liquid leaking from the reservoir itself. Liquid leaking from a device may be e-liquid that was incident on the heater but was not vaporized by the heater. Liquid that has been vaporized by the heater may condense within the device and form large droplets that then leak from the device. In particular, large droplets may form when the hot air and vapour from the heater meet the cooler internal surfaces of the device housing.

SUMMARY

At least one example embodiment relates to an aerosol-generating device.

In at least one example embodiment, an aerosol-generating device may include a housing, a reservoir, an atomizer, and a valve. The housing may include a first end defining a mouthpiece, a second end, and a cavity between the first end and the second end. The reservoir may be within the cavity and may be configured to store an aerosol-forming substrate. The valve may be within the mouthpiece of the housing. The valve may include a first side and a second side. The second side of the valve may include a hydrophilic coating, a hydrophobic coating, or both a hydrophilic coating and a hydrophobic coating.

In at least one example embodiment, the aerosol-generating device further includes an air inlet in the housing and an airflow channel. The airflow channel may extend from the air inlet, through the cavity, and to the mouthpiece. The valve may be in the airflow channel. The airflow channel may pass the atomizer.

In at least one example embodiment, the valve is a one-way valve. The valve may be configured to reduce the aerosol-forming substrate passing from the second side of the valve to the first side of the valve. The valve may include a hydrophobic coating.

In at least one example embodiment, the aerosol-generating device may further includes a storage tank configured to receive a portion of the aerosol-forming substrate repelled by the hydrophobic material of the coating of the valve.

In at least one example embodiment, the valve may be a ball valve, a duckbill valve, a diaphragm, an umbrella valve, or a hinged flap. The valve may be actuated via a draw on the mouthpiece of the aerosol-generating device. The valve may be actuated via a button on the housing. The valve may be at or near the first end of the housing and within the mouthpiece.

In at least one example embodiment, the atomizer includes a heater. The heater may include at least one heating element. The heater may be in communication with a wick. The wick may be configured to direct the aerosol-forming substrate from the reservoir to the at least one heating element.

In at least one example embodiment, the aerosol-generating device may further include a director configured to direct liquid resulting from condensation of aerosolized aerosol-forming substrate towards the at least one heating element.

In at least one example embodiment, the reservoir comprises an outer wall including a first face and a second face. The first face may be exposed to an airflow channel. The first face may be formed of hydrophobic material. The second face may be opposite the first face. The second face may be formed of a hydrophilic material. The outer wall may be in the airflow channel downstream of the atomizer.

BRIEF DESCRIPTION OF THE DRAWINGS

Example embodiments will now be described, by way of example only, with reference to the accompanying drawings.

FIG. 1 is a perspective view of an aerosol-generating device according to at least one example embodiment.

FIGS. 2A to 2E are views of an aerosol-generating device according to at least one example embodiment.

FIGS. 3A to 3G are views of an aerosol-generating device according to at least one example embodiment including an umbrella valve.

FIGS. 4A to 4E are views of an aerosol-generating device according to at least one example embodiment including a ball valve.

FIGS. 5A to 5C show layers applied to the walls of an airflow passage within an aerosol-generating device according to at least one example embodiment.

DETAILED DESCRIPTION

In at least one example embodiment, an aerosol-generating device comprises a housing having a first end defining a mouthpiece, a second end and a cavity defined between the first end and the second end. The device also comprises a reservoir within the cavity, for storing a liquid aerosol-forming substrate, and an atomizer. The device further comprises a valve within the mouthpiece of the housing, the valve having a downstream (or first) side and an upstream (or second) side. The second side of the valve includes one or more of a hydrophilic coating, a hydrophobic coating or a liquid absorbent coating.

The device may comprise an air inlet in the housing and an airflow channel from the air inlet, through the cavity to the mouthpiece. The valve may be in the airflow channel. The airflow channel may pass the atomizer Atomized liquid may be entrained within an airflow passing through the airflow channel.

As used herein, 'aerosol-generating device' relates to a device that interacts with an aerosol-forming substrate or an aerosol-generating article to generate an aerosol. An aerosol-generating device may comprise one or more devices used to supply energy from a power supply to an aerosol-forming substrate or an aerosol-generating article to generate an aerosol. An aerosol-generating device may comprise a power supply which may be an external power supply or an on-board power supply forming part of the aerosol-generating device. An aerosol-generating device may interact with an aerosol-forming substrate or an aerosol-generating article to generate an aerosol.

As used herein, the term 'aerosol-forming substrate' relates to a substrate capable of releasing volatile compounds that can form an aerosol. The volatile compounds may be released by heating the aerosol-forming substrate. The aerosol-forming substrate may be adsorbed, coated, impregnated or otherwise loaded onto a carrier or support. A suitable aerosol-forming substrate may comprise nicotine, a plant-based material, a homogenised plant-based material, at least one aerosol-former or other additives or ingredients, such as flavorants.

As used herein, 'downstream' is used to describe the relative position portions of the aerosol-generating device in relation to the direction of air flow through the device. The downstream (first) side of the valve may be closest to the mouthpiece in the direction of airflow and the upstream (second) side of the valve may be closest to the atomizer in the direction of airflow. In other words, air from the atomizer may be incident on the upstream side of the valve and air from the downstream side of the valve may be drawn through the mouthpiece. The aerosol-generating article may comprise a proximal end through which generated aerosol exits the aerosol-generating device. The proximal end may also be referred to as the mouthpiece end. The aerosol-generating device may be an elongate device, comprising a distal end opposite the proximal or mouth end. In such embodiments, the proximal end may be referred to as the downstream end. Similarly, as used herein, 'upstream' is used to describe the relative position of components, or portions of components, of the aerosol-generating device at the distal end of the aerosol-generating device.

As used herein, 'length' refers to the maximum longitudinal dimension between the upstream (second) end, in this case the base or closed end, of the device and the downstream (first) end or mouthpiece of the device.

The reservoir may be fixed within the housing of the aerosol-generating device. The reservoir may be refillable to allow for repeated vaping. In at least one example embodiment including a refillable reservoir, the housing of the aerosol-generating device may include an opening configured to allow aerosol-forming substrate to be inserted through the opening into the reservoir. Alternatively, the reservoir may be removable from the housing of the aerosol-generating device. A removable reservoir may be refilled once it has been removed from the housing. Alternatively, the removable reservoir may be a single use reservoir that is disposed of after depletion of the aerosol-forming substrate. A new reservoir may subsequently be inserted into the aerosol-generating device.

In at least one example embodiment, the reservoir is in fluid communication with the atomizer. The aerosol-forming substrate may be transported from the reservoir to the atomizer to be atomized. Transport may be provided by a wick or capillary element extending between the reservoir and the atomizer. The aerosol-forming substrate may be entrained in an airflow in the airflow channel to form an aerosol.

The valve may control the flow of fluid out of the aerosol-generating device. In at least one example embodiment, the valve reduces and/or prevents the exit of aerosol-forming substrate from the aerosol-generating device while allowing generated aerosol to exit via the mouthpiece.

A coating on the valve may further reduce the flow of large droplets of liquid through the valve. A coating may additionally, or alternatively, be provided on an downstream side of the valve, at the proximal end of the aerosol-generating device. The coating may be a hydrophilic coating, a hydrophobic coating, a liquid absorbent coating, a sub-combination thereof, or a combination thereof.

Liquid incident on a hydrophobic coating may be repelled. Having a hydrophobic coating on the upstream (second) side of the valve may repel liquid from the valve and the liquid may be retained within the housing of the aerosol-generating device. In this manner, liquid condensing within the housing and forming large droplets may be reduced and/or prevented from leaking through the valve. The hydrophobic coating may be at least partially formed of either polyurethane (PU) or a super-hydrophobic metal layer such as a micropore or mesh metal, such as copper or aluminium, functionalized with carbon chains to make them super-hydrophobic.

Liquid incident on a hydrophilic coating may be attracted to the coating. The coating may be on either an upstream (second) or downstream (first) side of the valve. A hydrophilic coating may attract liquid in the vicinity of the valve and reduce and/or prevent large droplets of liquid flowing through the valve or out of the device. The hydrophilic coating may be at least partially formed of 3 polyamide, polyvinyl acetate, cellulose acetate, cotton, a sub-combination thereof, or a combination thereof.

Liquid incident on a liquid absorbent coating may be absorbed into the coating. The coating may be on either an upstream (second) or downstream (first) side of the valve. Absorbing liquid into the coating may store liquid within the coating and reduce and/or prevent large droplets of liquid flowing out of the valve. The liquid absorbent coating may be at least partially formed of Nylon (polyamide), cellulose acetate, cotton cellulose, a sub-combination thereof, or a combination thereof.

Any combination of the hydrophobic, hydrophilic, and liquid absorbent coatings may be used.

In at least one example embodiment, the valve is a one-way valve configured to reduce and/or inhibit the flow of large droplets of liquid from the upstream (second) side of the valve to the downstream (first) side of the valve. The one-way valve, together with one or more coatings, may be configured to allow aerosol to move through the valve, while reducing and/or preventing large droplets of liquid from flowing out of the aerosol-generating device.

In some example embodiments, the valve includes a hydrophobic coating and the aerosol-generating device further comprises a storage tank. The storage tank may be configured to receive liquid repelled by the hydrophobic coating. In at least one example embodiment, liquid that has been repelled by the hydrophobic coating may be stored in the storage tank. The aerosol-generating device may further comprise a wick or a capillary element that is configured to direct liquid from the hydrophobic coating to the storage tank. The storage tank may be positioned within the housing of the aerosol-generating device. The storage tank may be fixed within the housing of the aerosol-generating device, and the housing may comprise an opening through which the storage tank can be emptied. Alternatively, the storage tank may be removable from the housing of the aerosol-generating device. The removable storage tank may be emptied once removed from the housing, such that it can be re-inserted into the housing and re-used. Alternatively, the removable storage tank may be disposable once removed from the housing. A new storage tank may then be inserted into the housing. The storage tank may be in fluid communication with the reservoir to allow liquid in the storage tank to return to reservoir for atomizing again.

The valve may be a ball valve. Alternatively, the valve may be a duckbill valve. Alternatively, the valve may be a diaphragm valve. Alternatively, the valve may be an umbrella valve. Alternatively, the valve may be a hinged flap. The valve may be any suitable one-way valve. A duckbill valve or an umbrella valve may be included.

In at least one example embodiment, the valve is actuated by a draw on the mouthpiece of the aerosol-generating device. Actuation of the valve may result in the valve opening such that fluid can flow from inside the housing of the aerosol-generating device out through the mouthpiece of the aerosol-generating device. Actuation as a result of a draw provides a device that is simple to operate because no additional actions are required. Actuation as a result of a draw may ensure that aerosol can pass through the valve. Actuation as a result of a draw may ensure that the valve remains in the closed position when the aerosol-generating device is not in use, such that liquid cannot escape through the valve when the aerosol-generating device is not in use.

Alternatively, or in addition, the valve may be actuated via a button on the housing. In this alternative embodiment, the valve is mechanically actuated. A mechanically actuated valve may provide a feeling of greater control when using the aerosol-generating device. A mechanically actuated valve may require manual actuation at the same time as a draw is initiated on the aerosol-generating device in order for generated aerosol to flow out of the device. The button may be located on a side of the housing of the aerosol-generating device, or on an end of the housing of the aerosol-generating device. The button to actuate the valve may be pressed simultaneous to a draw on the mouthpiece of the aerosol-generating device.

Alternatively, or in addition, the valve may be actuated by electrical signals. The electrical signals may be generated by a flow sensor positioned within the housing of the device and configured to detect a draw on the mouthpiece of the device. The flow sensor may be positioned downstream of the valve. The housing may include a bypass flow channel in which the flow sensor is located.

In at least one example embodiment, the valve is positioned at or near the proximal end of the housing. In at least one example embodiment, the valve is positioned within the mouthpiece. Providing a valve in the mouthpiece of the aerosol-generating device may allow the valve to reduce and/or minimize leakage of both liquid that has leaked from the reservoir and liquid produced by condensation upstream of the atomizer in the housing of the aerosol-generating device. Minimizing and/or reducing the length of housing positioned downstream of the valve may also reduce and/or minimize the space in which aerosol can further condense to form liquid.

In at least one example embodiment, the atomizer may comprise a heater. A heater may vaporize liquid aerosol-forming substrate to form a vapour. The vapour may cool to form condensed liquid droplets within the airflow, forming an aerosol. Alternatively, the atomizer may be a mechanical atomizer, including a piezoelectric element. In this alternative embodiment, the piezoelectric element may vibrate in response to an alternating current being passed through the piezoelectric element. Vibrations of the piezoelectric element may force the liquid aerosol-forming substrate through a nozzle assembly such that droplets of the liquid aerosol-forming substrate are formed. The droplets are entrained in the airflow in the airflow channel to form an aerosol.

In at least one example embodiment, the heater may comprise one or more heating elements. The heating element may be a planar heating element, a heater rod, a heater coil, or any other suitable heating element configuration. The heating element may be formed of an electrically resistive material such that passing an electric current through the heating element causes the heating element to produce heat. The heating element may be directly electrically coupled to a heat source. Suitable electrically resistive materials include semiconductors such as doped ceramics, for example doped silicon carbides, electrically 'conductive' ceramics such as molybdenum disilicide, carbon, graphite, metals, metal alloys, and composite materials made of a ceramic material and a metal material. Alternatively, or in addition, the heating element may comprise a susceptor and the heater may further comprise an inductor located to induce a current to heat the susceptor. For example, the inductor may comprise a coil arranged outside a heating chamber, or surrounding a heating chamber, that acts to induce heating currents in the susceptor.

The heater may be in communication with a wick. The wick may be configured to direct liquid from the reservoir to the heater. The wick may direct liquid aerosol-forming substrate from the reservoir to the heater. The wick may be at least partially formed of a material able to absorb liquid aerosol-forming substrate. Such a material may be a porous, fibrous, spongy, foam or capillary material. The wick may comprise a bundle of capillaries. The wick may comprise a plurality of fibers. The wick may comprise fine-bore tubes. The wick may comprise a combination of fibers, threads and fine-bore tubes. The fibers, thread and fine-bore tubes may be generally aligned to convey liquid to the electric heater. Such a material may have a desired (or, alternatively, pre-defined) capillarity. Examples of suitable materials to absorb liquid aerosol-forming substrate include ceramic- or graphite-based materials in the form of fibers or sintered powders. Examples of suitable materials also include sponge or foam materials, foamed metal or plastics materials, a fibrous material, for example made of spun or extruded fibers, such as cellulose acetate, polyester, or bonded polyolefin, polyethylene, terylene or polypropylene fibers, nylon fibers or ceramic.

Wicks of different porosities may be used to accommodate different liquid physical properties such as density, viscosity, surface tension and vapour pressure. The wick may have a first end positioned within the reservoir and a second end terminating at the heater. Alternatively, the second end of the wick may be surrounded by the heater. For example, if the heating element is a coil heating element then the coil may be wrapped around the second end of the wick. The second end of the wick is typically positioned within an airflow path within the housing of the aerosol-generating device so that air is drawn past the wick and entrains the vapor. The vapor may subsequently cool to form an aerosol and/or vapor.

In at least one example embodiment, the aerosol-generating system may also include a director configured to direct liquid resulting from condensation of aerosolised liquid aerosol-forming substrate towards the heater. The director may be positioned within the housing of the device. The director may be positioned external to each of the reservoir and the atomizer. The director may be a wicking member or a capillary element or any device configured to transport liquid to the atomizer Directing the liquid to the atomizer may allow the liquid to be aerosolized or re-aerosolized, so that accumulation within the housing may be reduced.

In at least one example embodiment, the reservoir of the aerosol-generating device comprises an outer wall having a first face exposed to the airflow channel in the housing and formed of hydrophobic material. The reservoir may further comprise a second face opposite the first face and formed of a hydrophilic material. The outer wall of the reservoir may be positioned adjacent the airflow channel downstream of the atomizer With this arrangement liquid condensed on the outer wall may be transported into the reservoir through the outer wall, and escaping of liquid in the reservoir via the outer wall may be reduced.

The airflow channel downstream of the atomizer may comprise walls having a first layer, in contact with aerosol in the airflow channel, comprising a hydrophobic material and a second layer, underneath the first layer, comprising a hydrophilic material.

In at least one example embodiment, the aerosol-generating system may further comprise a power supply and a control unit. The power supply may provide power to the heater. The heater is configured to heat an aerosol-forming substrate. With this arrangement an aerosol can be generated. The control unit may control the power supplied from the power supply to the heater. The control unit may control the temperature generated and the duration of the heating. The control unit may control other characteristics of the heater.

Figure 1:
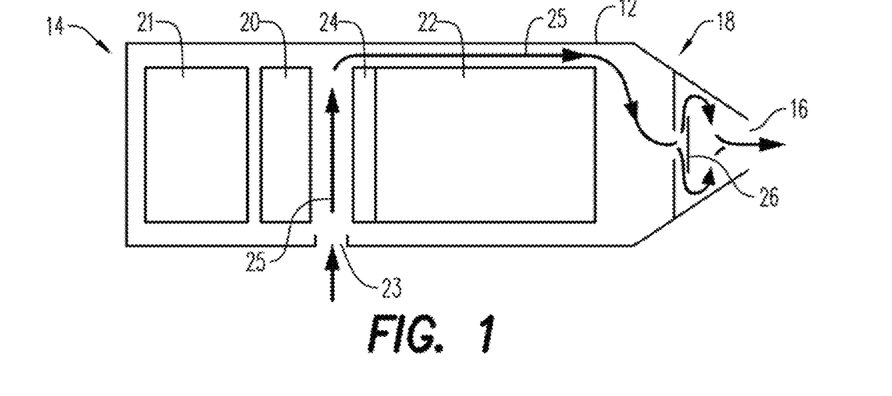

FIG. 1 is a schematic representation of an aerosol-generating device 10. The aerosol-generating device 10 comprises a housing 12 with a distal end 14 and a proximal end 16. The housing 12 at the proximal end 16 narrows to define a mouthpiece 18. Within the housing 12 is a power supply 21, a control unit 20, a reservoir of liquid aerosol-forming substrate 22, an atomizer 24, and a valve 26. An air flow channel 25 is defined within the housing 12, such that air can be drawn through the housing 12 from an air inlet 23 to the mouthpiece 18 and through the valve 26. A draw on the mouthpiece 18 draws air through the air inlet 23 and through or past the atomizer 24 such that aerosolized droplets of the aerosol-forming substrate 22 are entrained in the air flow. The air flow then passes out of the valve 26 and through the mouthpiece.

The power supply 21 and the control unit 20 may be contained in a reusable portion of the device 10, and the atomizer 24, the reservoir 22, and the mouthpiece 18 may be part of a consumable portion of the device 10 that is attached to the reusable portion.

Figure 2A:
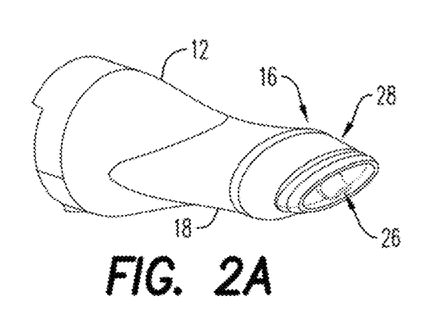
Figure 2B:
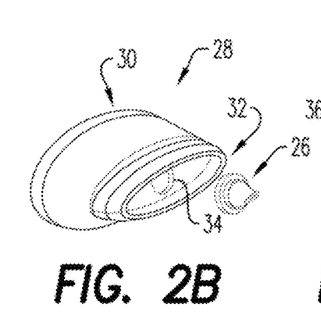

FIGS. 2A to 2E are illustrations of at least one example embodiment of an aerosol-generating device 10. The valve 26 shown in FIG. 2A is a duckbill valve. As shown, a proximal end 16 of the mouthpiece 18 of the housing 12 is covered by a valve connector 28. The valve connector 28 has a distal open end 30 and a proximal closed end 32 as shown in FIG. 2B. The open end 30 is shaped to slide over the proximal end 16 of the housing 12 and be retained in position covering the proximal end 16. The closed end 32 includes an aperture 34. The duckbill valve 26 is located within the aperture 34 of the valve connector 28.

Figure 2C:
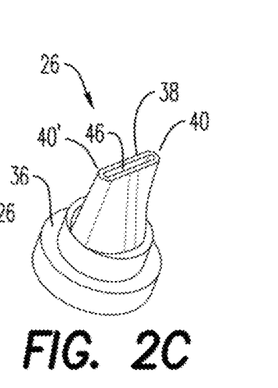

FIG. 2C shows the duckbill valve 26 alone. The duckbill valve 26 comprises a valve seat 36 and a nozzle 38. A channel 42, shown in FIG. 2D, runs through the nozzle 38, defined by inner walls 50 of the nozzle. The channel 42 extends from an opening 44 in the valve seat 36 to an opening 46, shown in FIG. 2D, in the nozzle 38 defined by opposing sides 40 and 40', shown in FIG. 2C. When in position, the channel 42 of the duckbill valve 26 aligns with the air flow channel 25 of the device 10 as shown in the cut through views of FIGS. 2D and 2E.

Figure 2D:
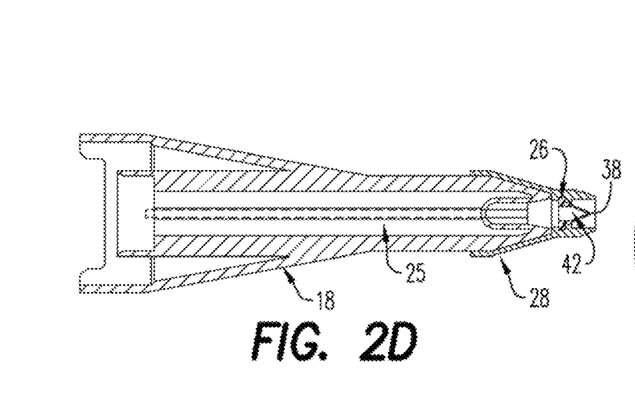

The nozzle 38 may be formed of a rubber or elastomer material such that the nozzle 38 is deformable. The nozzle 38 is shaped such that when no force is applied to the nozzle 38, opposing sides 40 and 40' of the nozzle 38 are in contact and the opening 46 of the nozzle is in a closed position. In the closed position, the opposing sides 40 and 40' of the nozzle 38 reduce and/or prevent liquid such as e-liquid or condensed aerosol escaping through the valve 26 when there is no draw on the device. When air is drawn through the channel 42 from the valve seat 36 to the nozzle 38, air pressure inside the nozzle 38 forces the opposing sides 40 and 40' apart, such that air can escape through the opening 44.

Figure 2E:
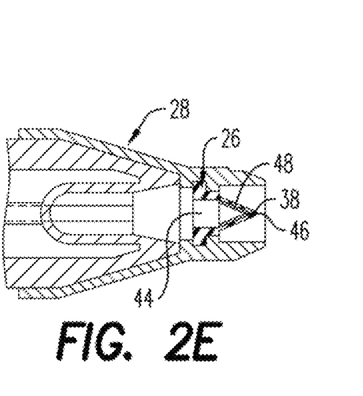

The duckbill valve 26 includes an inner coating 48, shown in FIG. 2E. The inner coating 48 is a hydrophobic coating. The coating 48 covers substantially the entirely of the inner wall 50 of the nozzle 38. The coating 48 repels liquid, such as e-liquid or condensed aerosol. When a draw is initiated on the device 10 and the nozzle 38 is brought into the open position, liquid is reduced and/or prevented from escaping through the opening 46 as the coating 48 repels the liquid so that the liquid cannot pass through the nozzle 38. In this way, the coating 48 reduces and/or prevents liquid leaking from the mouthpiece 18.

FIGS. 3A to 3G illustrate at least one example embodiment of an aerosol-generating device 10. The valve 26 may be an umbrella valve. In at least one example embodiment, a proximal end 16 of the mouthpiece 18 of the housing 12 is covered by a valve connector 28. Again, other example embodiments, the valve connector 28 shown in FIGS. 3A to 3G has a distal open end 30 and a proximal closed end 32. The open end 30 is shaped to slide over the proximal end 16 of the mouthpiece 18 and be retained in position covering the proximal end 16. In at least one example embodiment, the closed end 32 includes a central aperture 54 and two side apertures 56 and 56' shown in FIG. 3G. The side apertures 56 and 56' are coaxial with the air channel 25 of the device 10 as shown in the cut through views of FIGS. 3D and 3E.

Figures 3A, 3B:
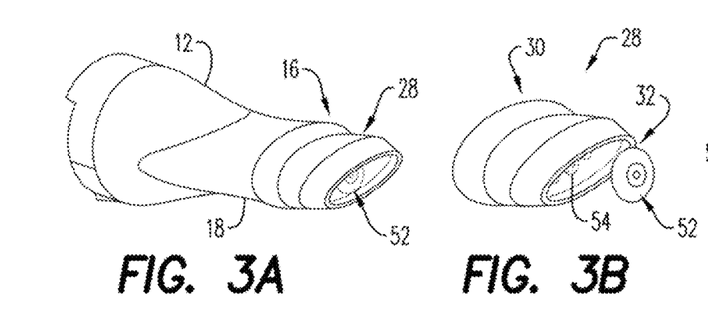
Figure 3C:
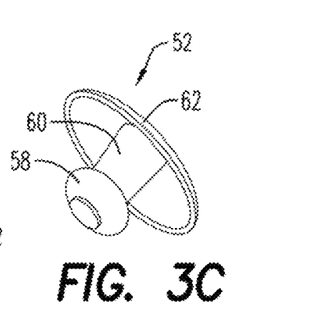
Figure 3D:
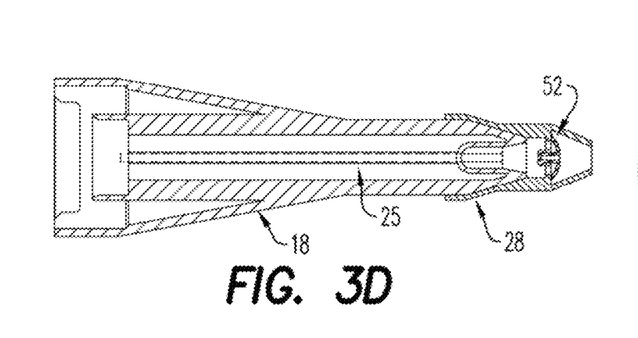
Figure 3E:
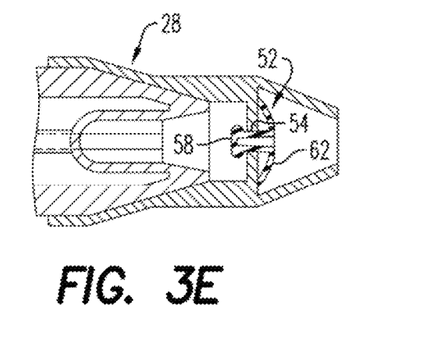

FIG. 3C illustrates the umbrella valve 52 alone. The umbrella valve 52 comprises a valve plug 58, a valve neck 60 and an umbrella portion 62. The valve neck 60 runs between the valve plug 58 and the umbrella portion 62. The valve neck 56 is positioned within the central aperture 54 of the closed end 32 of the valve connector 28. The valve plug 58 is located on an upstream side of the closed end 32. The umbrella portion 62 is located opposite the valve plug 58 on a downstream side of the closed end 32. The umbrella portion 62 is a concave circular portion, extending downwards from the end of the valve neck 60 towards the valve plug 58.

The valve plug 58 has an external circumference larger than the internal circumference of the central aperture 54. Therefore, the valve plug 58 is prevented from passing through the central aperture 54.

Figure 3F:
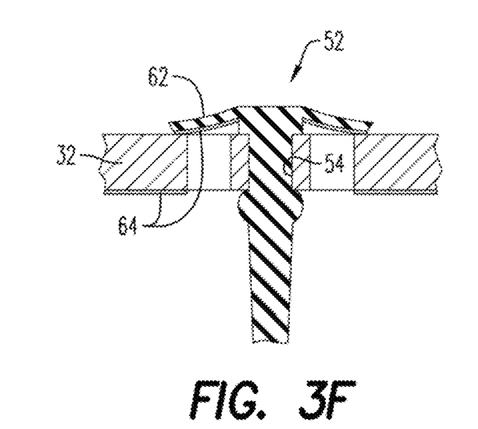

The umbrella portion 62 has an external circumference such that it extends over each of the side apertures 56 and 56' in a closed position as shown in FIG. 3F. In the closed position, escape of liquid is through the valve 26 when there is no draw on the device 10 is reduced and/or prevented. The umbrella portion 62 is formed of a rubber or elastomer material such that the umbrella portion 62 is deformable. When air is drawn through the device 10, air pressure on the upstream side of the umbrella portion 62 from air passing through the side apertures 56 and 56' forces the umbrella portion 62 to deform and invert, such that the umbrella portion 62 no longer covers the side apertures 56 and 56' such that air can pass through the valve 26 as shown in FIG. 3G.

Figure 3G:
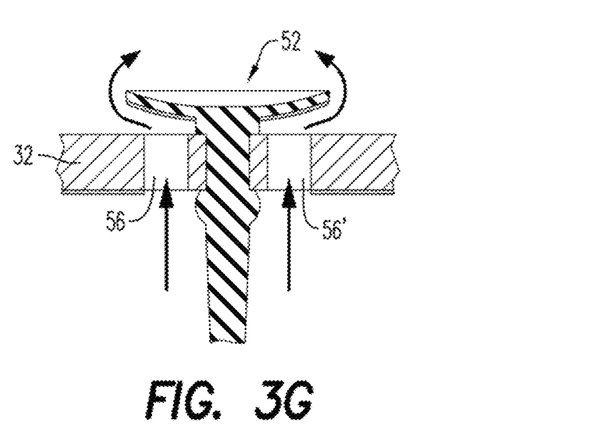

The umbrella valve 52 includes an inner coating 64, shown in FIGS. 3F and 3G. The inner coating 64 may be a hydrophobic coating. The coating 64 is located both on the upstream side of the closed end 32 and on the upstream side of the umbrella portion 62. The coating 64 repels liquid, such as e-liquid or condensed aerosol. When a draw is taken on the device 10 and the umbrella portion 62 is inverted such that the side apertures 56 and 56' are uncovered, escape of liquid through the side apertures 56 and 56' is reduced and/or prevented as the coating 64 repels the liquid. In this way, the coating 64 reduces and/or prevents liquid leaking from the mouthpiece 18.

FIGS. 4A to 4E illustrate views of at least one example embodiment of an aerosol-generating device 10. The valve 26 is an ball valve. In at least one example embodiment, a proximal end 16 of the mouthpiece 18 of the housing 12 is covered by a valve connector 28. The valve connector 28 has a distal open end 30 and a proximal closed end 32. The open end 30 is shaped to slide over the proximal end 16 of the mouthpiece 18 and be retained in position covering the proximal end 16.

Figure 4A:
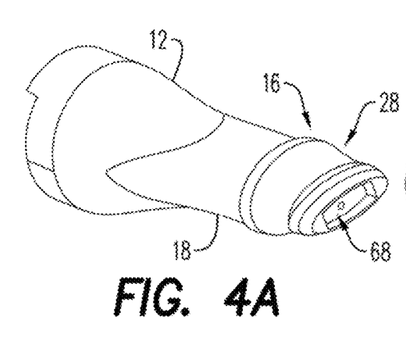
Figure 4B:
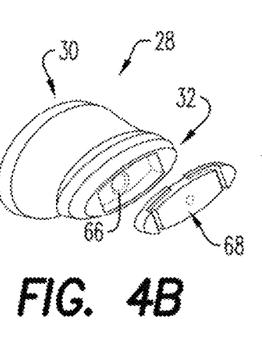
Figure 4C:
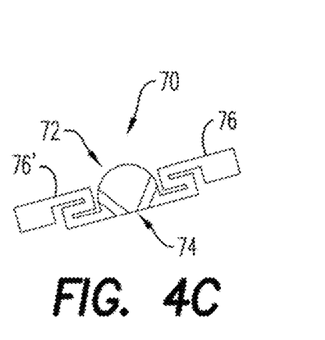
Figure 4D:
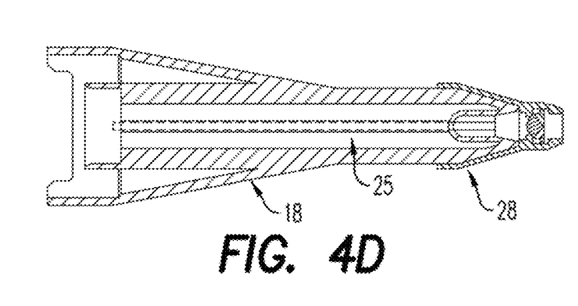

In at least one example embodiment, the closed end 32 includes an aperture 66. The aperture 66 is aligned with the air channel 25 of the device 10 as shown in the cut through views of FIGS. 4D and 4E. FIG. 4B shows a perspective front view of a valve portion 68 to be positioned over the closed end 32 of the valve connector 28. FIG. 4C shows a side view of the valve portion 68 alone.

The valve portion 68 includes a central ball element 70. The ball element 70 has an upstream side 72 that is rounded. The ball element 70 has a downstream side 74 that is flattened. Extending radially outwards from opposing sides of the downstream side 74 of the ball element 70 are wing portions 76 and 76'. The wing portions 76 and 76' are each formed of a bent planar sheet. The sheet is bent to form a 'zig-zag' shape when viewed from the side in FIG. 4C.

In position, the wing portions 76 and 76' abut the closed end 32 of the valve connector 28 and the ball element 70 is positioned within the aperture 66. The ball element 70 blocks the aperture 66 and reduces and/or prevents liquid such as e-liquid or condensed aerosol from escaping through the valve 26.

The wing portions 76 and 76' are formed of a resilient material, such as rubber or elastomer material, such that the wing portions 76 and 76' are deformable. The 'zig-zag' shape of the wing portions 76 and 76' allow the wing portions 76 and 76' to act like a spring. If the wing portions 76 and 76' are deformed by an applied force, the wing portions 76 and 76' will return to their original position when the force is removed. When air is drawn through the device 10, air pressure on the upstream side 72 of the ball element 70 pushes the ball element 70 away from the aperture 66 and the wing portion 76 and 76' deform. The ball element 70 no longer covers the aperture 66 such that air can pass through the valve 26.

Figure 4E:
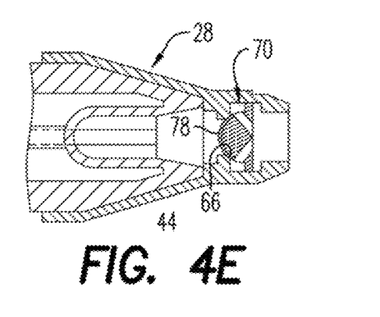

The ball valve 52 includes an inner coating 78, shown in FIG. 4E. The inner coating 78 is a hydrophobic coating. The coating 78 is located on the upstream side 72 of the ball element 70. The coating 78 repels liquid, such as e-liquid or condensed aerosol. When there is a draw on the device 10, the ball element 70 is drawn away from the aperture 66, and escape of liquid through the aperture 66 is reduced and/or preventedas the coating 78 repels the liquid. In this way, the coating 78 reduces and/or prevents liquid leaking from the mouthpiece 18.

Figure 5A:
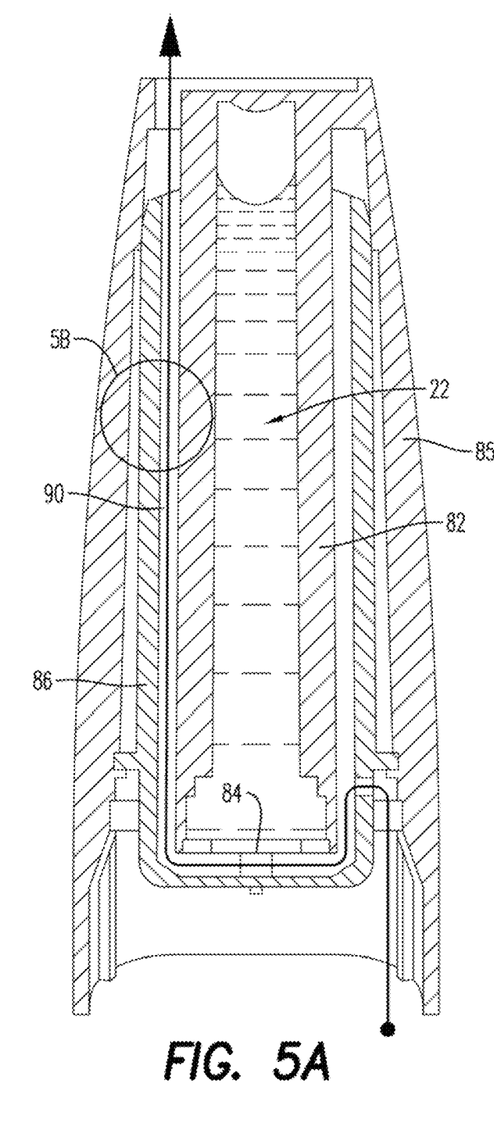
Figure 5B:
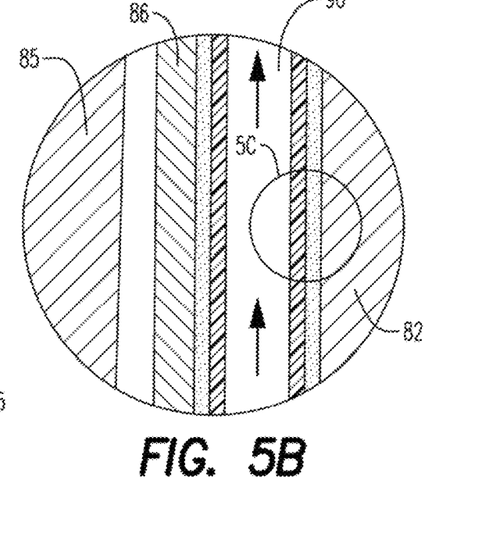
Figure 5C:
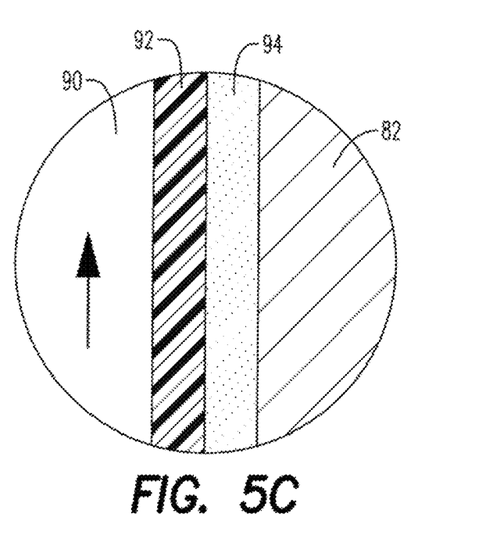

FIGS. 5A, 5B, and 5C illustrate the airflow channel through a consumable portion of an aerosol-generating device of the type shown in FIG. 1. The consumable portion comprises an outer housing 85 and an inner housing 86. Within the inner housing 86 is a reservoir 22 having an outer wall 82. The reservoir 22 holds an aerosol-forming substrate 80, such as a liquid aerosol-forming substrate. A mesh heater 84 is provided at the base of the reservoir 22, which, in operation, vaporizes liquid from the reservoir 22. The vapor can escape into the airflow channel 90. The airflow channel 90 extends from an inlet, through the housing to a mouthpiece, including a valve as described.

The walls of the airflow channel 90 are provided with two different membranes in a layered structure, illustrated in FIG. 5B and FIG. 5C. FIG. 5C is an enlargement of a portion of FIG. 5B, in which the two layers can most clearly be seen. The underlying layer 94 is a hydrophilic layer. The overlying layer 92, which is in contact with the aerosol in the airflow channel 90, is hydrophobic. This combination of layers acts a diode for liquid flow, so that liquid condensed onto the hydrophobic layer is transported efficiently to the hydrophilic layer but liquid does not pass from the hydrophobic layer back to hydrophilic layer. If the outer wall of the reservoir is made fluid permeable underneath these layers, for example by forming apertures through it, or is replaced entirely by these layers, then liquid condensing in the airflow channel downstream of the heater can be effectively returned to the reservoir.

We claim:

1. An electronic vaping device comprising:
   a housing having a first end and a second end;
   a mouthpiece at a first end of the housing;
   a vaporizer in the housing; and
   a valve within the mouthpiece, the valve including a hydrophilic coating, a hydrophobic coating, or both a hydrophilic coating and a hydrophobic coating.

2. The electronic vaping device of claim 1, wherein the housing defines a cavity between the first end and the second end thereof.

3. The electronic vaping device of claim 2, further comprising:
   a reservoir in the cavity, the reservoir configured to store an aerosol-forming substrate.

4. The electronic vaping device according to claim 3, wherein the reservoir includes
   an outer wall including, a first face exposed to an airflow channel, the first face formed of a hydrophobic material, and a second face opposite the first face, the second face formed of a hydrophilic material.

5. The electronic vaping device according to claim 4, wherein the outer wall is in the airflow channel and between the vaporizer and the mouthpiece.

6. The electronic vaping device of claim 3, further comprising:

an air inlet in the housing; and an airflow channel extending from the air inlet, the valve in the airflow channel.

7. The electronic vaping device according to claim 6, wherein the airflow channel passes the vaporizer.

8. The electronic vaping device according to claim 1, wherein the valve is a one-way valve.

9. The electronic vaping device according to claim 1, wherein:

the valve includes a hydrophobic coating; and the electronic vaping device further comprises, a storage tank configured to receive a portion of an aerosol-forming substrate repelled by the hydrophobic coating.

10. The electronic vaping device according to claim 1, wherein the valve is a ball valve, a duckbill valve, a diaphragm, an umbrella valve, or a hinged flap.

11. The electronic vaping device according claim 1, wherein the valve is actuated via a draw on the mouthpiece.

12. The electronic vaping device according to claim 1, wherein the valve is actuated via a button on the housing.

13. The electronic vaping device according to claim 1, wherein the vaporizer includes a heater and a wick.

14. The electronic vaping device according to claim 1, further comprising:

a director configured to direct liquid resulting from condensation of vaporized aerosol-forming substrate towards the vaporizer.

* * * * *